(12) United States Patent
Stoffel et al.

(10) Patent No.: US 6,740,512 B1
(45) Date of Patent: May 25, 2004

(54) NEUTRAL SPHINGOMYELINASE

(75) Inventors: Wilhelm Stoffel, Cologne (DE); Kay Hofmann, Cologne (DE); Stephan Tomiuk, Cologne (DE)

(73) Assignee: Memorec Biotec GmbH, Cologne (DE)

( * ) Notice: Subject to any disclaimer, the term of this patent is extended or adjusted under 35 U.S.C. 154(b) by 0 days.

(21) Appl. No.: 09/485,473

(22) PCT Filed: Aug. 11, 1998

(86) PCT No.: PCT/EP98/05127

§ 371 (c)(1),
(2), (4) Date: Feb. 11, 2000

(87) PCT Pub. No.: WO99/07855

PCT Pub. Date: Feb. 18, 1999

Related U.S. Application Data

(60) Provisional application No. 60/078,386, filed on Mar. 18, 1998.

(30) Foreign Application Priority Data

Aug. 11, 1997 (DE) .......................... 197 34 764
Oct. 15, 1997 (DE) .......................... 197 58 501

(51) Int. Cl.[7] ................................. C12N 9/00
(52) U.S. Cl. ..................................... 435/183
(58) Field of Search .......................... 435/183

(56) References Cited

U.S. PATENT DOCUMENTS 5,919,687 A * 7/1999 Chatterjee et al. .......... 435/199

FOREIGN PATENT DOCUMENTS

WO    WO 9828445 A    7/1998

OTHER PUBLICATIONS

Chatterjee S. & Ghosh N.: "Neutral sphingomyelinase from human urine" J. Biol. Chem., vol. 264, No. 21 (Jul. 25, 1999), pp. 12554–12561.

Kostellow A. et al.: "Reduction in Extracellular MG2+ Induces Sphingomyelinase, Elevates Ceramide and Releases NF–KB in Aortic Smooth Muscle Cells", FASEB Journal, vol. 10, No. 6 (Apr. 30, 1996), p. A1253.

Cai Z. et al.: Alteration of the sphingomyelin/ceramide pathway is associated with resistance of the human breast carcinoma MCF7 cells to Tumor Necrosis Factor alpha–mediated cytotoxicity, J. Biol. Chem., vol. 272, No. 11 (Mar. 14, 1997).

Database Genbank, Accession No. AA412649 (May 18, 1997), Hillier et al.: "H. sapiens cDNA clone Image 730457—EST.".

Tomiuk S. et al.: "Cloned mammalian neutral sphingomyelinase: functions in sphyngolipid signaling?", Prc. Natl. Acad. Sci. USA, vol. 95, No. 7 (Mar. 31, 1998), pp. 3638–3643.

* cited by examiner

Primary Examiner—Patrick J. Nolan
(74) Attorney, Agent, or Firm—Jacobson Holman PLLC

(57) ABSTRACT

The present invention relates to eukaryotic neutral sphingomyelinase (nSMase) and its application.

9 Claims, 12 Drawing Sheets

FIG. 1-1 human neutral Sphingomyelinase (NSM) Gene Sequence

```
     ACCGCGGCCGTCGCTGGAGAGTTCGAGCCGCCTAGCGCCCCTGGAGCTCCCCAACCATGA
   1 ------------------------------------------------------------ 60
     TGGCGCCGGCAGCGACCTCTCAAGCTCGGCGGATCGCGGGGACCTCGAGGGGTTGGTACT
                                                                  E I

AGCCCAACTTCTCCCTGCGACTGCGGATCTTCAACCTCAACTGCTGGTGAGTGCGTCTGC
  61 ------------------------------------------------------------ 120
     TCGGGTTGAAGAGGGACGCTGACGCCTAGAAGTTGGAGTTGACGACCACTCACGCAGACG

GGAGTGCGGTCTGGGGGCCACCTTCCGTTCGCACCCATGCAGCCTTCCTCCCCTATCCC
 121 ------------------------------------------------------------ 180
     CCTCACGCCAGACCCCCGGTGGAAGGCAAGCGTGGGTACGTCGGAAGGAGGGGATAGGG

GCCCCACGATCTCAGGGTGTAGGGAAAACCCGAACCTCCAAAGTCCACATCTGGCCCCAG
 181 ------------------------------------------------------------ 240
     CGGGGTGCTAGAGTCCCACATCCCTTTTGGGCTTGGAGGTTTCAGGTGTAGACCGGGGTC

CGCCGGTGGTCCCAGCAGTCGCCTCCCCTGCCCCGCTCTTCCCTTCCTTAGGGGCATTCC
 241 ------------------------------------------------------------ 300
     GCGGCCACCAGGGTCGTCAGCGGAGGGACGGGGCGAGAAGGGAAGGAATCCCCGTAAGG

GTACTTGAGCAAGCACCGGGCCGACCGCATGAGGCGCCTGGGAGACTTTCTGAACCAGGA
 301 ------------------------------------------------------------ 360
     CATGAACTCGTTCGTGGCCCGGCTGGCGTACTCCGCGGACCCTCTGAAAGACTTGGTCCT
                                                                  E II

GAGCTTCGACCTGGCTTTGCTGGAGGAGGTGAGATTGTGCAGCACGGTGCGGAACCCAGG
 361 ------------------------------------------------------------ 420
     CTCGAAGCTGGACCGAAACGACCTCCTCCACTCTAACACGTCGTGCCACGCCTTGGGTCC

CTGGGAGGAGGGACAGACCGTCCCACTGGGGAAAGACCAAGCAGGCATCCTCACCGCTTC
 421 ------------------------------------------------------------ 480
     GACCCTCCTCCCTGTCTGGCAGGGTGACCCCTTTCTGGTTCGTCCGTAGGAGTGGCGAAG

CCTCAGGTGTGGAGTGAGCAGGACTTCCAGTACCTGAGACAGAAGCTGTCACCTACCTAC
 481 ------------------------------------------------------------ 540
     GGAGTCCACACCTCACTCGTCCTGAAGGTCATGGACTCTGTCTTCGACAGTGGATGGATG
                                                                  E III

CCAGCTGCACACCACTTCCGGAGGTGAGAAGCCCACTGGCCTGAAGCCTGTTGTCATCCC
 541 ------------------------------------------------------------ 600
     GGTCGACGTGTGGTGAAGGCCTCCACTCTTCGGGTGACCGGACTTCGGACAACAGTAGGG

AGGAGGCTCTTGGCCCTGCCAGCCCTTCCCTATCCTGCCTGCACTCTCCAGTCTCCTCCA
 601 ------------------------------------------------------------ 660
     TCCTCCGAGAACCGGGACGGTCGGGAAGGGATAGGACGGACGTGAGAGGTCAGAGGAGGT

GCCTCCTCTCCCTCTGGATGTGAGAGAAGGAGAAGGGTGAACCAAGAAGGTCCTATGACT
 661 ------------------------------------------------------------ 720
     CGGAGGAGAGGGAGACCTACACTCTCTTCCTCTTCCCACTTGGTTCTTCCAGGATACTGA

TCAGCCCCTTTCAGCTTTGTTTTCTGGCTGCCCTATACTCCTCCAAAGGCCGTCGCCTTG
 721 ------------------------------------------------------------ 780
     AGTCGGGGAAACTCGAAACAAAAGACCGACGGGATATGAGGAGGTTTCCGGCAGCGGAAC

GTTCTAGGGCTAGTCCCAGCAGTAGAAAAGAAAAAAATAGCTGATCAGAGCTGCAAGAC
 781 ------------------------------------------------------------ 840
     CAAGATCCCGATCAGGGTCGTCATCTTTTTCTTTTTTTATCGACTAGTCTCGACCTTCTG

AAGGGAGGCGAAGAAGGCTGGGTGTCTCTCCCTGTTTTTCTGGTTATTAAGCAGGGCTTG
 841 ------------------------------------------------------------ 900
     TTCCCTCCCCTTCTTCCGACCCACAGAGAGGGACAAAAAGACCAATAATTCGTCCCGAAC
```

FIG. 1-2

```
      CTCTCCCTCCTTCTCCCCCACATCCTAGCATGAGCCAATGATTCCCTTAGGGCTCTGAGG
1861 ------------------------------------------------------------ 1920
      GAGAGGGAGGAAGTGGGGGTGTAGGATCGTACTCGGTTACTAAGGGAATCCCGAGACTCC
                                                                    E VIII
      AAGGCAACACAATGGTACCCAAGAACTGNTACGTCAGCCAGCAGGAGCTGAAGCCACCCT
1921 ------------------------------------------------------------ 1980
      TTCCGTTGTGTTACCATGGGTTCTTGACNATGCAGTCGGTCGTCCTCGACTTCGGTGGGA

CCTTTGGTGTCCGCATTGACTACGTGCTTTACAAGGTCAGGCTCCTCCCTTCAACATGCT
1981 ------------------------------------------------------------ 2040
      GGAAACCACAGGCGTAACTGATGCACGAAATGTTCCAGTCCGAGGAGGGAAGTTGTACGA

TTCATATGCTGTGTCTCTTTGTCTAACCTGTGTAGATCCTCCTTTGCTCAGNTAGTCTAG
2041 ------------------------------------------------------------ 2100
      AAGTATACGACACAGAGAAACAGATTGGACACATCTAGGAGGAAACGAGTCNATCAGATC

TCTTGGACCACTGATGGGTGGAAAGTGGGGTAGCCGGGAGCTGGTTCTCTGGGAAGAGGC
2101 ------------------------------------------------------------ 2160
      AGAACCTGGTGACTACCCACCTTTCACCCCATCGGCCCTCGACCAAGAGACCCTTCTCCG

CCTCATATATAAGCTTCTCTNTGGCCCTTACTTTTCCTAGGCAGTTTCTGGGTTTTACAT
2161 ------------------------------------------------------------ 2220
      GGAGTATATATTCGAAGAGANACCGGGAATGAAAAGGATCCGTCAAAGACCCAAAATGTA

CTCCTGTAAGAGTTTTGAAACCACTACAGGCTTTGACCCTNACAGGGGCACCCCCCTCTC
2221 ------------------------------------------------------------ 2280
      GAGGACATTCTCAAAACTTTGGTGATGTCCGAAACTGGGANTGTCCCCGTGGGGGAGAG

TTGATCATGAAGCCCTGATGGCTACTCTGTTTGTGAGGCACAGCCCCCACAGCAGAACC
2281 ------------------------------------------------------------ 2340
      AACTAGTACTTCGGGACTACCGATGAGACAAACACTCCGTGTCGGGGGTGTCGTCTTGG

CCAGCTCTACCCACGGTGAGTCACCCCCACCCTTTCCTTGGCCCTTGCCCCGCTTGAAGC
2341 ------------------------------------------------------------ 2400
      GGTCGAGATGGGTGCCACTCAGTGGGGGTGGGAAAGGAACCGGGAACGGGGCGAACTTCG

AGCCCTTCCACTCTTGACTCTCTCCTGCCCCACTGCCCTGCTCTGTTGTAGGACCAGCAG
2401 ------------------------------------------------------------ 2460
      TCGGGAAGGTGAGAACTGAGAGAGGACGGGGTGACGGGACGAGACAACATCCTGGTCGTC

AGAGGTCGCCGTTGATGTGTGTGCTAAAGGAGGCCTGGACGGAGCTGGGTCTGGGCATGG
2461 ------------------------------------------------------------ 2520
      TCTCCAGCGGCAACTACACACACGATTTCCTCCGGACCTGCCTCGACCCAGACCCGTACC

CTCAGGCTCGCTGGTGGGCCACCTTCGCTAGCTATGTGATTGGCCTGGGGCTGCTTCTCC
2521 ------------------------------------------------------------ 2580
      GAGTCCGAGCGACCACCCGGTGGAAGCGATCGATACACTAACCGGACCCCGACGAAGAGG
                                                                    E IX
      TGGCACTGCTGTGTGTCCTGGCGGCTGGAGGAGGGCCGGGGAAGCTGCCATACTGCTCT
2581 ------------------------------------------------------------ 2640
      ACCGTGACGACACACAGGACCGCCGACCTCCTCCCCGGCCCCTTCGACGGTATGACGAGA

GGACCCCCAGTGTAGGGCTGGTGCTGTGGGCAGGTGCATTCTACCTCTTCCACGTACAGG
2641 ------------------------------------------------------------ 2700
      CCTGGGGGTCACATCCCGACCACGACACCCGTCCACGAAAGATGGAGAAGGTGCATGTCC

AGGTCAATGGCTTATATACGGCCCAGGCTGAGCTCCAGCATGTGCTAGGAAGCGCAAGGG
2701 ------------------------------------------------------------ 2760
      TCCAGTTACCGAATATATGCCGGGTCCGACTCGAGGTCGTACACGATCCTTCGCGTTCCC

AGGCCCAGGATCTGGGCCCAGAGCCTCAGCCAGCCCTACTCCTGGGGCAGCAGGAGGGG
2761 ------------------------------------------------------------ 2820
      TCCGGGTGGTAGACCCGGGTCTCGGAGTCGGTCGGGATGAGGACCCCGTCGTCCTCCCC

ACAGAACTAAAGAACAATAAAGCTTGGCCCAA
```

FIG. 2-1
Mouse Neutral Sphingomyelinase (nSMase) gene sequence

```
    TNGANNCTGTTAGCTCCAGNCCGGTNGGTCGCCCGTNCTAGNCNNATCTNTATAGCTCTTC
  1 ------------+------------+------------+------------+------------+------------+ 60
    ANCTNNGACAATCGACGTCNGGCCANCCAGCGGCANGATCNGNNTAGANATATCGAGAAG

GTTGCGAGCNCAATTNNNTCTCAATAAANGGATNCANCCCTATGACAGAACGTGGACCCC
 61 ------------+------------+------------+------------+------------+------------+ 120
    CAACGCTCGNGTTAANNNAGAGTTATTTNCCTANGTNGGGATACTGTCTTGCACCTGGGG

CGCCCGCCANCNCANGNGANACCGCGGCATGGGNCTGAGGTGCNCANGGTGTCTGGGGCG
121 ------------+------------+------------+------------+------------+------------+ 180
    GCGGGCGGTNGNGTNCNCTNTGGCGCCGTACCCNGACTCCACGNGTNCCACAGACCCCGC

AGGGGTTACCTCAGCGATGGTCTTTGACACCTGAAAGCTGGAGCTTTTGAANAGCCCCAN
181 ------------+------------+------------+------------+------------+------------+ 240
    TCCCCAATGGAGTCGCTACCAGAAACTGTGGACTTTCGACCTCGAAAACTTNTCGGGGTN

CACCTTCAGCTTCAGGGGCGGCTCNGGCGGCAACCGCACGTGANATGCTGGGGGCTTCGA
241 ------------+------------+------------+------------+------------+------------+ 300
    GTGGAAGTCGAAGTCCCCGCCGAGNCCGCCGTTGGCGTGCACTNTACGACCCCCGAAGCT

CTTGGGCCGGCACGGNTGCTGGGTGGCCATGGAANNNNACAGNACAGAGCCGGNACACAA
301 ------------+------------+------------+------------+------------+------------+ 360
    GAACCCGGCCGTGCCNACGACCCACCGGTACCTTNNNNTGTCNTGTCTCGGCCNTGTGTT

ATANTGCGAGTCGCCANGGNAACCGCGTGGCTCCTCCCCGAACGCCCNCAAGGGGCGGGA
361 ------------+------------+------------+------------+------------+------------+ 420
    TATNTCGCTCAGCGGTNCCNTTGGCGCACCGAGGAGGGGCTTGCGGGNGTTCCCCGCCCT

CCTGAGTGAGTTCNTGGGCGGGGCCTCNCATCAACTTCAAGCCTGTTGCTGGTGGAAGCC
421 ------------+------------+------------+------------+------------+------------+ 480
    GGACTCACTCAAGNACCCGCCCCGGAGNGTAGTTGAAGTTCGGACAACGACCACCTTCGG
E I
    GAGCCGGGAACAAGGGAGGAACCTGTAGGCCGCGGTGCGGATAACCCACCGAAGGACCTA
481 ------------+------------+------------+------------+------------+------------+ 540
    CTCGGCCCTTGTTCCCTCCTTGGACATCCGGCGCCACGCCTATTGGGTGGCTTGGTGGAT
E I
    AGAATCTGGAACAGTCCACCCGAGATTCCTTCCAGGACTGCCGGCGGACTCTCGCATTCA
541 ------------+------------+------------+------------+------------+------------+ 600
    TCTTAGACCTTGTCAGGTGGGCTCTAAGGAAGGTCCTGAGGGCCGCCTGAGAGCGTAAGT

GCCCGGGATTTGCAGCCGACCTTCTTTCCGGGTGGAATGACGGCCTTTGTCCCAGTAACG
601 ------------+------------+------------+------------+------------+------------+ 660
    CGGGCCCTAAACGTCGGCTGGAAGAAAGGCCCACCTTACTGCCGGAAACAGGGTCATTGC

CAGGAGTCNNCCCCACCCCCAACCAGCTCGCGTTCCTGGGTCGGGGCAGCGCAGGATAGG
661 ------------+------------+------------+------------+------------+------------+ 720
    GTCCTCAGNNGGGGTGGGGGTTGGTCGAGCGCAAGGACCCAGCCCCGTCGCGTCCTATCC
                                                                    Start
    GCATAAGCCTGTGCGCGCAAATCCGCCTCGCCGCCCTTGCTCCGAAGCACTCCAGCCATG
721 ------------+------------+------------+------------+------------+------------+ 780
    CGTATTCGGACACGCGCGTTTAGGCGGAGCGGCGGGAACGAGGCTTCGTGAGGTCGGTAC AAGCTCAACTTTTCTCTACGGCTGAGAGTTTTCAATCTCAACTGCTGtaagtaagtgct
781 ------------+------------+------------+------------+------------+------------+ 840
    TTCGAGTTGAAAAGAGATGCCGACTCTCAAAAGTTAGAGTTGACGACcattcattcacga
```

FIG. 2-2

```
     cccaggcgtgggCTGCAGCCGTCGGAGCCACCTTCCAGTCCCCTCTCGCACATGCCTAGGA
841  ------------------------------------------------------------ 900
     gggtccgcaccccGACGTCGGAGCCTCGGTGGAAGGTCAGGGGAGAGCGTGTACGGATCCT AGGAAGCAGGTCTTCTTCAGCCGAGCTAGACCCTGTCCTTCCCGAACCACCAAAGTCCAC
901  ------------------------------------------------------------ 960
     TCCTTCGTCCAGAAGAAGTCGGCTCGATCTGGGACAGGAAGGGCTTGGTGGTTTCAGGTG ATCGCCTAAAGACCAGAGCTTGGGTGGTTGCAGCAATCACCAAAGTCCCTATCATCCAAA
961  ------------------------------------------------------------ 1020
     TAGCGGATTTCTGGTCTCGAACCCACCAACGTCGTTAGTGGTTTCAGGGATAGTAGGTTT GCTGAGGTGATGACAGCAGTAATCGTCCCAAACCTGGCCCATGTCTTTCCTTTTAAATGA
1021 ------------------------------------------------------------ 1080
      CGACTCCACTACTGTCGTCATTAGCAGGGTTTGGACCCGGTACAGAAAGGAAAATTTACT TTTACTTTTATTTTATGTACATTTGGTGTTTTGCCTGTATGTATGTCTGTGTGAAGGTCC
1081 ------------------------------------------------------------ 1140
      AAATGAAAATAAAATACATGTAAACCACAAAACGGACATACATACAGACACACTTCCACG CAGATTCTCTGGAACTGGAGTTACAGACAGTTGTAAGCTGTCATGTGCTTGCTGGAAATT
1141 ------------------------------------------------------------ 1200
      GTCTAAGAGACCTTGACCTCAATGTCTGTCAACATTCGACAGTACACGAACGACCTTTAA GAACTGCTGACCCATCTCTTCTGCCCCCTGCGTCCTCCACCCCTTTTAGGGACATCCCCT
1201 ------------------------------------------------------------ 1260
      CTTGACGACTGGGTAGAGAAGACGGGGGACGCAGGAGGTGGGGAAAATCCCTGTAGGGGA ACCTGAGCAAACATAGGGCGGACCGCATGAAGCGCTTGGGAGACTTTCTGAACTTGGAAA
1261 ------------------------------------------------------------ 1320
      TGGACTCGTTTGTATCCCGCCTGGCGTACTTCGCGAACCCTCTGAAAGACTTGAACCTTT
  E II
      ACTTTGATCTGGCTCTCCTGGAGGAGGTGAGGTTGTAGGGCAGGCTAGGTTGGAGGAGGG
1321 ------------------------------------------------------------ 1380
      TGAAACTAGACCGAGAGGACCTCCTCCACTCCAACATCCCGTCCGATCCAACCTCCTCCC CAGCAGGCGGCAGGCGGCGGCAGGAAAACTTGTTCTGTCTTGGGATGAAATCCCAAGCAA
1381 ------------------------------------------------------------ 1440
      GTCGTCCGCCGTCCGCCGCCGTCCTTTTGAACAAGACAGAACCCTCCTTTAGGGTTCGTT GTATCCTCACCTTCTTCCTCCAGGTGTGGAGTGAGCAGGACTTCCCAGTACCTAAGGCAA
1441 ------------------------------------------------------------ 1500
      CATAGGAGTGGAAGAAGGAGGTCCACACCTCACTCGTCCTGAAGGGTCATGGATTCCGTT
  E III
      AGGCTATCGCTCACCTATCCAGATGCACACTACTTCAGAAGGTGAAAAGCCTGTGTTCTC
1501 ------------------------------------------------------------ 1560
      TCCGATAGCGAGTGGATAGGTCTACGTGTGATGAAGTCTTCCACTTTTCGGACACAAGAG AGCCTGTTCTCAGACGAGGAAGCTCTCCAACATTCTTGCTTGCACCCTCGATCTTCTTCC
1561 ------------------------------------------------------------ 1620
      TCGGACAAGAGTCTGCTCCTTCGAGAGGTTGTAAGAACGAACGTGGGAGCTAGAAGAAGG TCTGGGTCTGAGAAGAGCAGGCCGTCACCCTCATCTTGCAAGGGCTGCTGTCTTAGGCTT
1621 ------------------------------------------------------------ 1680
      AGACCCAGACTCTTCTCGTCCGGCAGTGGCAGTAGAACGTTCCCGACGACAGAATCCGAA TGTTCTGGGGTTGATCTTAGCAGTAGAGCTGGGAGACCGCGGAGGGGAAGAGGGCTGGCT
1681 ------------------------------------------------------------ 1740
      ACAAGACCCCAACTAGAATCGTCATCTCGACCCTCTGGCGCCTCCCCTTCTCCCGACCGA
```

FIG. 2-3

```
     GGGTACTCCCCTCCTTGCTCTTCTGGTTATTAAGCAAGAGTTGGTTTTCAGCGGGATGAT
1741 ------------+------------+------------+------------+------------+------------ 1800
     CCCATGAGGGGAGGAACGAGAAGACAAATAATTCGTTCTCAACCAAAAGTCGCCCTACTA
E IV
     AGGCAGTGGCCTCTGTGTGTTCTCCAAACACCCAATCCAGGAAATCTTCCAGCATGTCTA
1801 ------------+------------+------------+------------+------------+------------ 1860
     TCCGTCACCGGAGACACACAAGAGGTTTGTGGGTTAGGTCCTTTAGAAGGTCGTACAGAT

CAGTCTGAATGGTTACCCCTACATGGTAAGGATCTCTTCCCTATCCTTGCTAACACAGAC
1861 ------------+------------+------------+------------+------------+------------ 1920
     GTCAGACTTACCAATGGGGATGTACCATTCCTAGAGAAGGGATAGGAACGATTGTGTCTG

TGGACGCAGCCTTCCTGGGGCCTTGGCAGGAGGGTGTCAGTACCCTGAGTTTTGTCTTC
1921 ------------+------------+------------+------------+------------+------------ 1980
     ACCTGCGTCGGAAGGACCCCGGAACCGTCCTCCCACAGTCATGGGACTCAAAACAGAAG

TCTTGCCTGCAGTTCCATCATGGAGACTGGTTCTGTGGGAAGTCTGTGGGCTGCTGGTG
1981 ------------+------------+------------+------------+------------+------------ 2040
     AGAACGGACGTCAAGGTAGTACCTCTGACCAAGACACCCTTCAGACACCCCGACGACCAC
E V
     CTCCGTCTAAGTGGACTGGTGCTCAATGCTACCGTGACTCATGTGAGTGGGGCTAGCCAG
2041 ------------+------------+------------+------------+------------+------------ 2100
     GAGGCAGATTCACCTGACCACGTGTTACGATGGCACTGAGTACACTCACCCCGATCGGTC

GCTTAGGCAGTGGGTCAAGCAGCCCAATGCTATGGTGGAGAAGAGACGCCACTAGTTAGT
2101 ------------+------------+------------+------------+------------+------------ 2160
     CGAATCGGTCACCCAGTTCCTCGGGTTACGATACCACCTCTTCTCTGCGGTGATCAATCA

TCTGCTGCCTGGGGATAAGGCATGGGATCAGAAGCTAGCATTGGGCAAGCGTTCACCCATT
2161 ------------+------------+------------+------------+------------+------------ 2220
     AGACGACGGACCCCTATTCCGTACCCTAGTCTTCGATCGTAACCCGTTCCAAGTGGGTAA

CCCTGTCACACTCTGCCATGTGACAGATGACAAGCTTGATTCAGACAGCCTTCTCTTTGA
2221 ------------+------------+------------+------------+------------+------------ 2280
     GGGACAGTGTGAGACGGTAGACTGTCTACTGTTCGAACTAAGTCTGTCGGAAGAGAAACT

TTTCACCTATTCCACTTTAGCTACATGCTGAGTACAGCCGACAGAAGGACATCTACTTTG
1281 ------------+------------+------------+------------+------------+------------ 2340
     AAAGTGGATAAGGTGAAATCGATGTACGACTCATGTCGGCTGTCTTCCTGTAGATGAAAC
E VI
     CACACCGTGTGGCCCAAGCTTGGGAACTGGCCCAGTTCATCCAGTGTGTGAGCCTGGGCT
2341 ------------+------------+------------+------------+------------+------------ 2400
     GTGTGGCACACCGGGTTCGAACCCTTGACCGGGTCAAGTAGGTCACACACTCGGACCCGA

TGATGGGGCTGTGGGGTGGGACGGGGTTGAGGGATGNGNAANTTATCCTTGAAGAGGG
2401 ------------+------------+------------+------------+------------+------------ 2460
     ACTACCCCCGAGTCCCCACCCCTGCCCCAACTCCCTACNCNTTNAATAGGAACTTCTCCC

CACATAATAAGGGAAGAATTTCCTCCTTGCCGCTCTTCCCCCAACTCAGCCACACATCCA
2461 ------------+------------+------------+------------+------------+------------ 2520
     GTGTATTATTCCCTTCTTCCCGGAGGAACGGCGAGAAGGGGGTTGAGTCGGTGTGTAGGT
E VII
     AGAATGCAGATGTGGTTCTATTGTGTGGAGACCTCAATATGCACCCCAAAGACCTGGGCT
2521 ------------+------------+------------+------------+------------+------------ 2580
     TCTTACGTCTACACCAAGATAACACACCTCTGGAGTTATACGTGGGGTTTCTGGACCCGA
```

FIG. 2-4

```
     GCTGCCTGCTGAAAGAGTGGACAGGGCTCCATGATGCTTTCGTTGAGACTGAGGACTTTA
2581 ------------------------------------------------------------ 2640
     CGACGGACGACTTTCTCACCTGTCCCGAGGTACTACGAAAGCAACTCTGACTCCTGAAAT

AGGTGAGAGACTGTTTCCCACCAACTCCACACTTGTTCCAGTCTTCCTGTCTCTTAGCAT
2641 ------------------------------------------------------------ 2700
     TCCAGTCTCTCACAAAGGGTGGTTGAGGTGTGAACAAGGTCAGAAGGACAGAGAATCGTA

CCTAGCCACCTGTTTCCCTAGGGCTCTGATGATGGCTGTACCATGGTACCCAAGAACTGC
2701 ------------------------------------------------------------ 2760
     GGATCGGTGGACAAAGGGATCCCGAGACTACTACCCACATGGTACCATGGGTTCTTGACG
E VIII
     TACGTCAGCCAGCAGGACCTGGGACCGTTTCCGTCTGGTATCCGGATTGATTACGTGCTT
2761 ------------------------------------------------------------ 2820
     ATGCAGTCGGTCGTCCTGGACCCTGGCAAAGGCAGTCCATAGGCCTAACTAATGCACGAA

TACAAGGTCAGGCTCTTATTCCCGGTGTGCCTTCTCCAGTATCTTCCTTCCTCTGTCACT
2821 ------------------------------------------------------------ 2880
     ATGTTCCAGTCCGAGAATAAGGGCCACACGGAAGAGGTCATAGAAGGAAGGAGACAGTGA

AGCCCACGCTTTAGTTCAGCTACAGTCTTGGGCCACTGATGGCTAAAGAATAGAATCCTG
2881 ------------------------------------------------------------ 2940
     TCGGGTGCGAAAGCAAGTCGATGTCAGAACCCGGTGACTACCGATTTCTTATCTTAGGAC

TCGGCTGGTTCTCTGGGAGAATTTAAGCTTCTCCATGTTCTTGCTCTTCCTAGGCAGTCT
2941 ------------------------------------------------------------ 3000
     AGCCGACCAAGAGACCCTCTTAAATTCGAAGAGGTACAAGAACGAGAAGGATCCGTCAGA

CTGAGTCCCACGTCTGCTGTGAGACTCTGAAAACCACTACAGGCTGTGACCCTCACAGTG
3001 ------------------------------------------------------------ 3060
     GACTCAGGGTGCAGACGACACTCTGAGACTTTTGGTGATGTCCGACACTGGGAGTGTCAC
E IX
     ACAAGCCCTTCTCTGATCACGAGGCCCTCATGGCTACTTTGTATGTGAAGCACAGCCCCC
3061 ------------------------------------------------------------ 3120
     TGTTCGGGAAGAGACTAGTGCTCCGGGAGTACCGATGAAACATACACTTCGTGTCGGGGG

CTCAGGAAGACCCCTGTACTGCCTGTGGTAAGCAGCATTTCCTTTGCCCCCTCTACTTTA
3121 ------------------------------------------------------------ 3180
     GAGTCCTTCTGGGGACATGACGGACACCATTCGTCGTAAAGGAAACGGGGAGATGAAAT

AGGCAGCCCCGCCTCCATCCTGACCCTCCCCTGCTCTACGTTCTCTCTTTTCCAGGCCC
3181 ------------------------------------------------------------ 3240
     TCCGTCGGGGCGGAGGTAGGACTGGGAGGGGACGAGATGCAAGAGAGAAAAGGTCCGGG

ACTGGAAAGGTCCGATTTGATCAGCGTGCTAAGGGAGGCCAGGACAGAGCTGGGGCTAGG
3241 ------------------------------------------------------------ 3300
     TGACCTTTCCAGGCTAAACTAGTCGCACGATTCCCTCCGGTCCTGTCTCGACCCCGATCC
E X
     CATAGCTAAAGCTCGCTGGTGGGCTGCATTCTCTGGCTATGTGATCGTTTGGGGGCTGTC
3301 ------------------------------------------------------------ 3360
     GTATCGATTTCGAGCGACCTCCCGACGTAAGAGACCGATACACTAGCAAACCCCCGACAG

CCTTCTGGTGTTGCTGTGTGTCCCGGCTGCAGGAGAAGAGGCCAGGGAAGTGGCCATCAT
3361 ------------------------------------------------------------ 3420
     GGAAGACCACAACGACACACAGGGCCGACGTCCTCTTCTCCGGTCCCTTTACCGGTACTA
```

FIG. 2-5

```
     CCTCTGCATACCCAGTGTGGGTCTGGTGCTGGTAGCAGGTGCAGTCTACCTCTTCCACAA
3421 ------------------------------------------------------------ 3480
     GGAGACGTATGGGTCACACCCAGACCACGACCATCGTCCACGTCAGATGGAGAAGGTGTT

GCAGGAGGCCAAGGGCTTATGTCGGGCCCAGGCTGAGATGCTGCACGTTCTGACAAGGA
3481 ------------------------------------------------------------ 3540
     CGTCCTCCGGTTCCCGAATACAGCCCGGGTCCGACTCTACGACGTGCAAGACTGTTCCCT

AACGGAGACCCAGGACCGAGGCTCAGAGCCTCACCTAGCCTACTGCTTGCAGCAGGAGG
3541 ------------------------------------------------------------ 3600
     TTGCCTCTGGGTCCTGGCTCCGAGTCTCGGAGTGGATCGGATGACGAACGTCGTCCTCC
                                     stop
     GGACAGAGCTTAAGAGCTTAACAATAAAACTTGCTTGACACACTCTAGTGGCTCTACCTT
3601 ------------------------------------------------------------ 3660
     CCTGTCTCGAATTCTCGAATTGTTATTTTGAACGAACTGTGTGAGATCACCGAGATGGAA GTTCCTTGCAGAGGCATGATGGGAACTGAAGGTCAGTGGCCTTGTCACTGTGTGGCTTTA
3661 ------------------------------------------------------------ 3720
     CAAGGAACGTCTCCGTACTACCCTTGACTTCCAGTCACCGGAACAGTGACACTCCGAAAT GAGCGTTGGCCTCTCACTTGCCTTTTTTGCACACTCCCGTCTCCTGCCAGCACAGAGCAT
3721 ------------------------------------------------------------ 3780
     CTCGCAACCGGAAAGTGAACGGAAAAAACGTGTGAGGGCAGAGGACGGTCGTGTCTCGTA AAACCCTGTTCATGGTCATAATCCTTTTATTGTAAACAACGAAGCCTCTGACTAAGCAGT
3781 ------------------------------------------------------------ 3840
     TTTGGGACAAGTACCAGTATTAGGAAAATAACATTTGTTGCTTCGGAGACTGATTGGTCA CCAGATGGCGGAGGTACAGCCCTTGTGATGGTGTCTTGCTTACGGGGCAGGGAGGCAGCT
3841 ------------------------------------------------------------ 3900
     GGTCTACCGCCTCCATGTCGGGAACACTGCGACAGAACGAATGCCCCGTCCCTCCGTCGA AACCATCATCTTCTAGCCCTGGGCTCCCATCTATGCAGGCATCTCTCTGAGCCTCCGTTC
3901 ------------------------------------------------------------ 3960
     TTGGTAGTAGAAGATCGGGACCCGAGGGTAGATACGTCCATCTAGAGACTCGGAGGCAAG CTCCTGGAATTGGNTCAGAGCAATCCCGCTTGGTTCACCAACCTCCAAACAGCTTCCTTA
3961 ------------------------------------------------------------ 4020
     GAGGACCTTAAGGNAGTCTCGTTAGGGCGAACCAAGTGGGTGGAGGTTTGTCGCCTTCCT AGGACCTGGTTTCTCAAAANGGNAAGGTNCGGGCCTCCGGTCTTCAATANGTTTTCCTAA
4021 ------------------------------------------------------------ 4080
     TCCTGGGCCAAAGAGTTTTNCCNTTCCANCGGGGGTGGCCAGAAGTTATNCAAAAGGATT AAAGGGANGAATGAAAANCCTTAAGNNCCAACAAGGGGAACCCTTGGNCCCAAAAGGGGA
4081 ------------------------------------------------------------ 4140
     TTTCCCTNCTTACTTTTNGGAATTCNNGGTTGTTCCCCTTGGGAACCNGGGTTTTCCCCT CCTGGGTGGTTTCCCNTTGGGGCCAAANTTATCCCAAAGGGGTCCAATTGAAGGGTTAAC
4141 ------------------------------------------------------------ 4200
     GGACCCACCAAAGGGNAACCCCGGTTTNAATAGGGTTTCCCCACCTTAACTTCCCAATTG CCCCCAAAAANNACCCNTTTCCCCCGGAATTTCCAAAGGTTTNCCCCCCCGGCAAAANC
4201 ------------------------------------------------------------ 4260
     GGGGGTTTTTNNTGGGNAAACGGGGCCTTAAAGGTTTCCAAANGGGGGGGCCGTTTTNG
```

FIG. 2-6

```
    TCCCTTGGGGNNCCNAANCCNTGGCCCGGNCTTGGCTTTTCCCCCTTTCCCAAGNATTTC
4261-----------+---------+---------+---------+---------+---------+4320
    AGGGAACCCCNNGGNTTNGGNACCGGGCCNGAACCGAAAAGGGGCAAAGGGTTCNTAAAG

AAANNTTCCCTNGGAAANCCCCTTGNTTGGNAAAACCNAATNANGAACCANGCCAANNNT
4321-----------+---------+---------+---------+---------+---------+4380
    TTTNNAAGGGANCCTTTNGGGGAACNAACCNTTTTGGNTTANTNCTTGGTNCGGTTNNNA

TGCCAANAAACCNTTTGGGCAAAGGGGGNAAATTCANCAANGGGGNAATTGGGGAAACCC
4381-----------+---------+---------+---------+---------+---------+4440
    ACGGTTNTTTGGNAAACCCGTTTCCCCCNTTTAAGTNGTTNCCCCNTTAACCCCTTTGGG

NTGGGTTTNCCCAAAGGGCCCNAANANT
4441-----------+---------+--------4468
    NACCCAAANGGGTTTCCCGGGNTTNTNA
``` mnSMase "konventional" Knock Out

FIG. 5

Constructs for generating transgenic mouse mutants

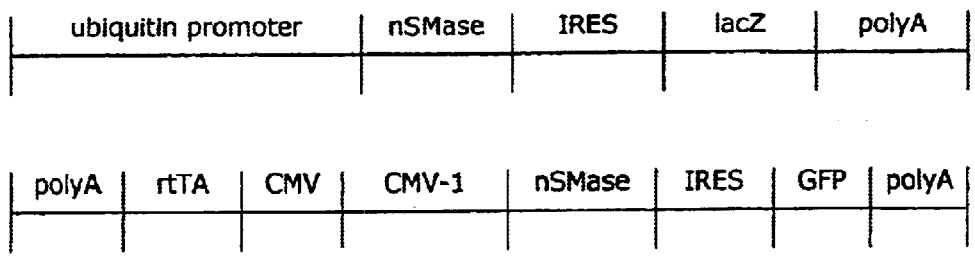

| Ubiquitin promoter: | regulatory sequence of the ubiquitin gene, controlling a ubiquitous transcription. |
| --- | --- |
| nSMase: | neutral sphingomyelinase |
| lacZ: | lacZ, gene coding for β-galactosidase |
| polyA: | recognition signal for the termination of transcription and polyadenylation |
| CMV: | cytomegalovirus promoter of the cytomegalovirus gene, controlling a ubiquitous transcription. |
| rtTA: | reverse transactivator, binds to the minimal promoter and thus controls transcription. The binding properties of the transactivator are influenced by tetracyclin. The addition of tetracyclin makes the transactivator bind to the minimal promoter and starts transcription, removal of tetracyclin prevents the binding of the transactivator to the minimal promoter and prevents transcription. |
| CMV-1: | minimal promoter, binding of transactivator starts transcription. |
| IRES: | *internal ribosomal entry sequence*, viral initiation signal for translation. |

NEUTRAL SPHINGOMYELINASE

This is a 371 of PCT/EP 98/05127 filed Aug. 11, 1998, which claims benefit under 35 USC 119(e) to U.S. provisional application No. 60/078,386, filed Mar. 18, 1998.

The present invention relates to nucleic acids coding for eukaryotic neutral sphingomyelinase, and applications thereof.

Sphingomyelin is an essential component of plasma membranes. Degradation of sphingomyelin gives a number of substances having potential second messenger properties, e.g., ceramide, sphingosine, sphingosine-1-phosphate. Two sphingomyelin-cleaving enzymatic activities are known, namely that of lysosomal acid sphingomyelinase, and that of plasma-bound neutral sphingomyelinase.

Bacterial neutral sphingomyelinase is a secreted soluble protein.

The present invention for the first time provides nucleic acids/coding for eukaryotic neutral sphingomyelinase. Eukaryotic neutral sphingomyelinase (nSMase) is characterized in that it cleaves sphingomyelin into ceramide and phosphocholine and that its activity depends on the addition of magnesium ions. It is a membrane-bound enzyme. Its maximum activity is achieved in the neutral pH range.

FIG. 5 shows constructs for obtaining transgenic mouse mutants.

Figures 1, 2, 3:
FIG. 1 shows the gene sequence of human neutral sphingomyelinase.
FIG. 2 shows the gene sequence of murine neutral sphingomyelinase.
FIG. 3 shows the results of the Northern and Western blotting of nSMase-overexpressing cell lines.
Figure 3:
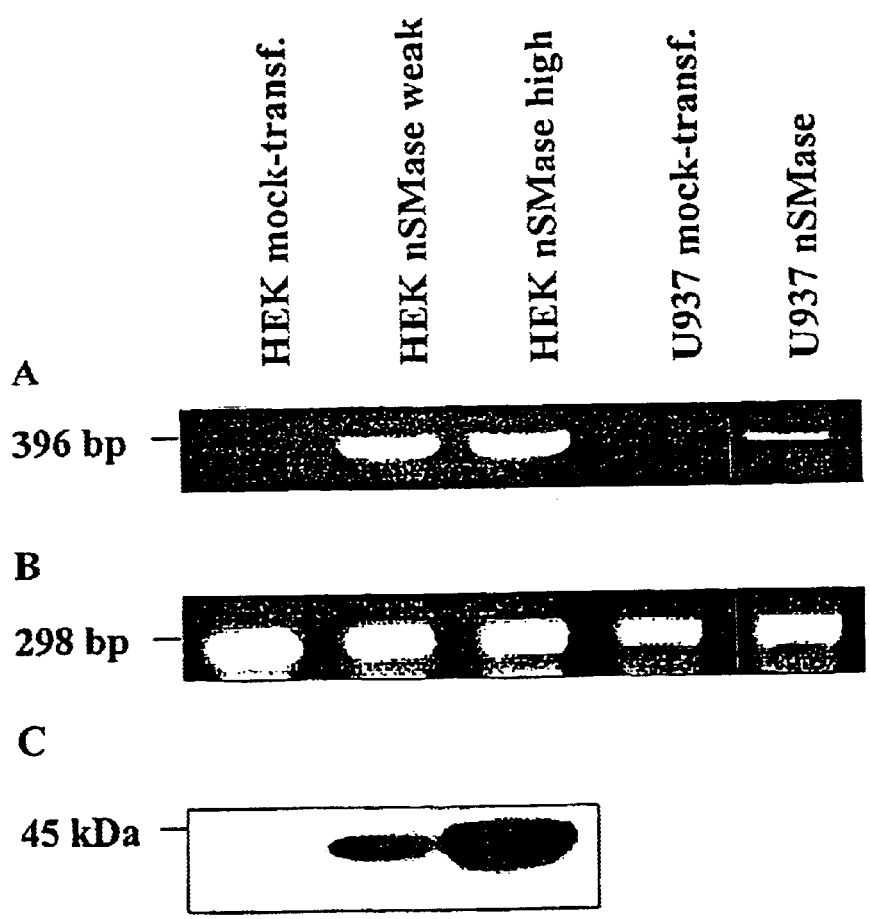

Preferably, the nucleic acid according to the invention is a nucleic acid coding for the neutral sphingomyelinase of a mammal. More preferably, it codes for human or murine neutral sphingomyelinase. The corresponding nucleic acid sequences are disclosed as SEQ. ID. NO. 3 and SEQ ID. NO. 4, respectively.

Parts of the nucleic acid sequences are identical with the EST sequences AA028477 and AA013912 (murine) and W32352 and AA056024 (human).

When he knows the amino acid and nucleic acid structure of human and murine neutral sphingomyelinase, one skilled in the art can easily detect the corresponding nucleic acids and proteins from other eukaryotes, considering the high homology between human and murine nSMases. To do this, he can either use cross-reacting antibodies for a purification by specific affinity chromatography, or he can synthesize oligonucleotide primers on the basis of the nucleic acid sequence and amplify the desired nucleic acids in a cDNA library of the eukaryote using polymerase chain reaction. The corresponding cDNA library can be obtained in a per se known manner by isolating mRNA from a tissue sample, followed by reverse transcription. From the nucleic acid sequence, the amino acid sequence can be derived by means of the genetic code. Alternatively, it is also possible to search for homologous sequences in EST (expressed sequence tags) data bases and combine them.

The nucleic acids according to the invention are suitable for the expression of eukaryotic neutral sphingomyelinase in prokaryotic or eukaryotic systems. In addition, they are also suitable for expression of nSMase in vivo in a gene therapy, or especially, in the form of fragments with complementary structures, they are also suitable as antisense nucleotides for reducing the expression of nSMase.

The nucleic acids according to the invention can be prepared by chemical synthesis or by amplification in genetically engineered organisms by methods per se known to those skilled in the art.

The invention also relates to eukaryotic neutral sphingomyelinase obtainable by the expression of the nucleic acids according to the invention.

The nSMase according to the invention can be prepared by expression in genetically engineered organisms. Eukaryotic expression systems are particularly suitable. Appropriate eukaryotic expression systems are to those skilled in the art, for example, pRc/CMV (Stratagene). Purification from genetically engineered organisms offers an easy and direct access to the nSMase according to the invention, especially in the case of overexpression, and in addition allows for the isolation thereof in larger quantities.

The eukaryotic neutral sphingomyelinase is preferably a mammal, especially human or murine, neutral sphingomyellnase. The amino acid sequences of the human and murine neutral sphingomyelinases are represented as SEQ. ID. NOS. 1 and 2.

The molecular weights of human and murine sphingomyelinases are 47.6 and 47.5 kDa, respectively. In contrast to bacterial nSMases, the mammal nSMases according to the invention do not contain a signal sequence at the N terminus. From the hydrophobicity analysis, it can be considered that two neighboring hydrophobic membrane domains at the C terminus are separated by eight amino acids. Therefore, the proteins appear to be integral membrane proteins whose catalytically active domain is directed towards the cytosol while only a small proportion of the enzymes contacts the extracellular environment. This is in contrast to bacterial nSMases which are secreted, soluble proteins, but in agreement with previous studies on the properties of neutral sphingomyelinases of mammals. According to a Northern blot analysis, the 1.7 kb mRNA of murine nSMase is expressed in all tissues. In the kidneys, brain, liver, heart and lungs, the Northern blot shows a strong signal while expression in the spleen appears to be low. This measurement was not in agreement with the measured enzymatic activities of the corresponding tissues. This speaks in favor of a post-transcriptional regulation of nSMase.

The pH optimum of the neutral sphingomyelinase according to the invention is within a range of from 6.5 to 7.5, with a $K_m$ value for C18 sphingomyelin within a range of from 1.0 to $1.5 \times 10^{-5}$ M. The activity is dependent on the presence of magnesium ions; the addition of EDTA results in an inhibition of SMase activity, which can be restored, however, by the addition of $Mn^{2+}$ or $Mg^{2+}$ ions. The addition of 0.3 to 0.5% Triton X-100 increases the enzymatic activity. The activity is not affected by a treatment with DTT or 2-mercaptoethanol whereas the addition of 20 mM glutathione led to inhibition. The activity of nSMase is not restricted to sphingomyelin; the structurally related phosphatidylcholine was also cleaved with about 3% activity.

Also claimed are variants of the eukaryotic neutral sphingomyellnase. The term "variants" encompasses both naturally occurring allelic variations of the eukaryotic neutral sphingomyelinase and proteins prepared by recombinant DNA technology (especially by in-vitro mutagenesis using chemically synthesized oligonucleotides) followed by expression which correspond to eukaryotic neutral sphingomyellnase in terms of biological and/or immunological activity. This may include the deletion, insertion or conservative substitution of amino acids. "Conservative substitutions" means that an amino acid is substituted by another amino acid having similar physicochemical properties.

Thus, for example, the following amino acids are interchangeable: serine and alanine; alanine and glycine; methionine and serine; lysine and arginine; lysine and serine.

In particular, the term "variants" also includes N-terminally and/or C-terminally truncated proteins as well as acetylated, glycosylated, amidated and/or phosphorylated derivatives.

At least part of the activity of nSMase seems to reside in the C-terminal region since the fragment 1-282 of murine nSMase failed to exhibit an increase of sphingomyelinase activity when expressed in HEK293 cells. This invention also relates to C-terminal fragments of nSMase. Compounds in which nSMase or its variants are coupled with other molecules, such as dyes, radionuclides or affinity components, are also variants according to the invention.

Also claimed are nucleic acids coding for eukaryotic neutral sphingomyelinase or being complementary to such nucleic acids. The nucleic acids may be, for example, DNA, RNA, PNA or nuclease-resistant analogues thereof. In particular, nuclease-resistant analogues include those compounds which have the phosphodiester linkage modified by hydrolysis-stable compounds, such as phosphothioates, methylphosphonates or the like.

Especially short fragments of the nucleic acids are suitable as antisense nucleotides. For reasons of specificity, they should preferably contain more than 6, more preferably more than 8 and most preferably more than 12 nucleotides. For reasons of diffusion and costs, they usually have a length of less than 30 nucleotides, preferably 24 or less, and more preferably 18 or less nucleotides.

The invention also relates to derivatives of nucleic acids which are coupled to other molecules for diagnostic or therapeutic purposes, for example, to fluorescent dyes, radioactive labels or affinity components, and fragments of the nucleic acids according to the invention, and the nucleic acids complementary to these nucleic acids, and variants of the nucleic acids. "Fragments" as used herein means nucleic acids truncated at the 5' or 3' or at both ends. The term "variants" means that these nucleic acids will hybridize with the nucleic acid according to the invention or with nucleic acids complementary thereto under stringent conditions. The term "stringent conditions" means that the hybridization is performed under conditions in which the temperature is even lower by up to 10° C. than the temperature (conditions being otherwise identical) just low enough for exactly complementary nucleic acids to anneal. For example, if an exactly complementary nucleic acid will anneal down to a temperature of about 55° C. under given conditions, then stringent conditions are temperatures of equal to or higher than 45° C. Preferably, the temperature range for stringent conditions is within 5° C., more preferably within 3° C.

Further, the invention relates to antibodies directed against the nSMase according to the invention or the nucleic acids according to the invention.

These substances are suitable, in particular, for use in diagnostics, in immuno-assays per se known to those skilled in the art, for histological studies and as medicaments for the treatment of conditions associated with an overexpression of nSMase. Such antibodies according to the invention can be obtained by methods per se known to those skilled in the art through immunization with nSMase, nucleic acids according to the invention or peptide and nucleic acid fragments in the presence of adjuvants.

Further, the invention relates to cell lines which overexpress the nSMase according to the invention. Such cell lines can be obtained by transfection with vectors containing the nucleic acids according to the invention coding for nSMase. In the case of eukaryotic cell lines, for example, transfection may be effected by electroporation. Preferably, the cell lines are stably transfected.

In this connection, "overexpression" means that the cell line has a higher activity of nSMase than cell lines which have not been transfected with the nucleic acids according to the invention. For example, suitable eukaryotic cell lines include the cell lines U937, HEK 293 or Jurkat.

In experiments, the cell lines exhibited a specific nSMase activity of between 0.3 and 10 $\mu$mol/mg of protein/hour.

FIG. 3 shows the Northern and Western blot analysis of nSMase expression in transfected cell lines. Portion A shows the result of a RT PCR of the whole cell RNA with primers hybridizing with human and murine nSMase cDNAs. Portion B shows the T PCR of the whole RNA with primers hybridizing with human β-actin cDNA as a control. Portion C shows the Western blot of the plasma membrane protein extract of different HEK 293 cell lines after SDS polyacrylamide gel electrophoresis and hybridization with polyclonal anti-nSMase antibodies.

The addition of 0.5 mM arachidonic acid resulted in a threefold increase of nSMase activity in the overexpressing HEK cells.

The invention further relates to a transgenic mammal which exhibits an overexpression (gain of function) or a genetic deficiency or defect (loss of function) for the nSMase according to the invention. The mammal is preferably a rodent, especially a mouse. Such transgenic mammals can be obtained by methods per se known to those skilled in the art and are especially suitable for elucidating the function of neutral sphingomyelinase. For transgenic mammals, defined gene constructs are injected into the pronucleus of a fertilized egg cell by DNA microinjection to achieve the expression of an additional gene. By selectively changing a gene in the genome of ES cells which are subsequently injected in blastocysts, the function of a gene is switched off.

Figure 4:
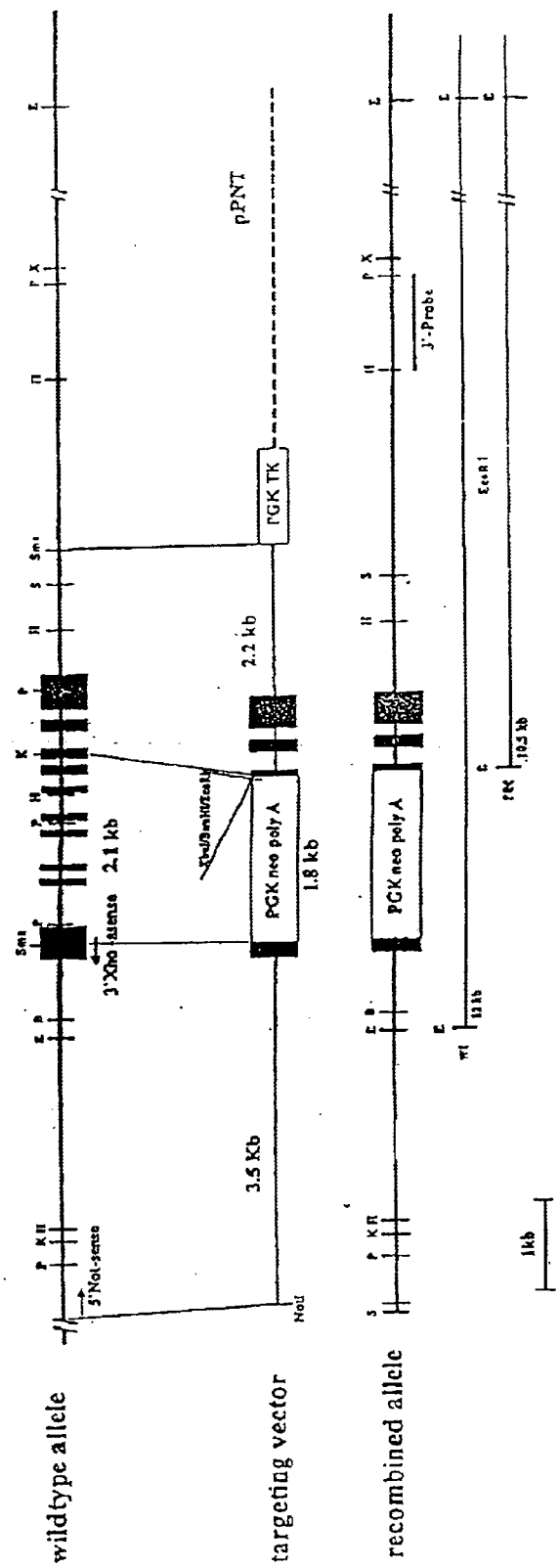
FIG. 4 shows the strategy for producing murine knockout mutants. The letters designate restriction sites.

The strategy and constructs for generating the mouse mutants are shown in FIGS. 4 and 5.

The transgenic animals are preferably animals in which the gene can be switched on and off temporally and in a tissue-specific way by external induction. Such transgenic mammals are especially suitable for elucidating the metabolic and signal transduction pathways related to the nSMase according to the invention; this in turn enables diagnostic or therapeutic applications. In particular, the transgenic mammals are suitable for the screening of pharmaceutically active substances.

The eukaryotic neutral sphingomyelinase according to the invention, the nucleic acids according to the invention and the antibodies according to the invention can be contained in medicaments and diagnostic agents, optionally together with further auxiliary agents. Such medicaments and diagnostic agents are suitable for the diagnosis and treatment of diseases based on over- or underexpression and/or an increased or reduced activity of eukaryotic neutral sphingomyelinase and/or disorders of cell proliferation, cell differentiation and/or apoptosis.

In particular, these are diseases in which inflammation processes, cell growth disorders and metabolic disorders are involved. For example, they may be cancers or disorders of cholesterol homeostasis (atherosclerosis).

A pharmaceutical screening method according to the invention relies on a change of the expression or activity of the nSMase according to the invention in nSMase-overexpressing cell lines upon the addition of at least one potential pharmaceutically active substance. Thus, the cell lines are suitable, in particular, for developing and testing pharmaceutical leading structures.

The invention will be further illustrated by the following Examples.

EXAMPLE 1

Cloning of the Nucleic Acid

The inventive nucleic acids coding for neutral sphingomyelinase were cloned into the NotI restriction sites of the cloning site of the eukaryotic expression vector pRc/CMV (Stratagene). The sequences of the resulting DNAs were obtained by sequencing using a Perkin-Elmer DNA sequencer 377A.

EXAMPLE 2

Cloning of the RNA

The whole RNA was isolated from different organs of eight three-week-old CD1 mice according to known methods, and poly(A$^+$) RNA was isolated by affinity purification on oligo(dT) cellulose (Boehringer Mannheim, Germany) according to standard methods.

EXAMPLE 3

Overexpressing Cell Lines

U937 cells were grown in PRMI 1640 medium with 10% fetal calf serum, 1 µg/ml penicillin/streptomycin and 0.03% glutamine at 37° C. and 5% $CO_2$. By electroporation with a Gene Pulser (Bio-Rad), 5×10$^6$ cells were transfected with 1 µg of linearized plasmid DNA coding for the nSMase according to the invention. The selection of stable clones was effected by using 1 mg/ml geneticin (G418, Life Technologies, Gaithersburg, Md.).

The nSMase purified from the cell lines exhibited a specific activity of between 0.3 and 10 µmol/mg of protein/ hour. Its pH optimum was at 6.5 and 7.5. The $K_M$ value for C18 sphingomyelin was from 1.0 to 1.5×10$^{-5}$ M. The activity was dependent on the presence of magnesium ions; the addition of EDTA inhibited the activity.

EXAMPLE 4

Measurement of nSMase Activity

The enzymatic activity was examined in cells and murine tissues. The cells were washed twice with ice-cold PBS and sedimented at 1,000×g. The pellet was resuspended in lysis buffer, and the cells were disrupted by repeated cycles of freezing and thawing. After centrifugation at 2,500×g for 2 min, extraction with lysis buffer containing 0.2% Triton X-100 was performed, followed by centrifugation at 100,000×g for 15 min.

Tissue from three-week-old mice was homogenized in cold lysis buffer. The quantity of protein or homogenized tissue to be examined was incubated with 10 nM (80,000 dpm) [N-$^{14}CH_3$]sphingomyelin for 30 min at 37° C. in a total volume of 200 µl. Then, 100 µl of water was added, and unreacted substrate was removed by extraction with chloroform-methanol (2:1, v/v). The radioactivity of the aqueous phase containing the enzymatically released phosphocholine was measured in a scintillation counter.

EXAMPLE 5

Polyclonal Antibodies

Rabbits were immunized with the synthetic peptide CDPHSDKPFSDHE (corresponding to amino acids 261 through 273 of murine nSMase), coupled to keyhole limpet hemocyanin. The polyclonal antibody serum was purified by chromatography on hydroxyapatite and affinity chromatography on a column having the above mentioned synthetic peptide bound thereto.

What is claimed is:

1. An isolated eukaryotic neutral sphingomyelinase comprising a sequence according to
   a) SEQ ID NO: 1 or SEQ ID NO: 2, or
   b) a variant of SEQ ID NO: 1 or SEQ ID NO: 2 having eukaryotic neutral sphingomyelinase enzymatic activity, wherein the variant is
      i) a naturally occurring allelic variation of SEQ ID NO: 1 or SEQ ID NO: 2, or
      ii) SEQ ID NO: 1 or SEQ ID NO: 2 having one inserted, deleted, or conservatively substituted amino acid, or
      iii) An N-terminally truncated or C-terminally truncated SEQ ID NO: 1 or SEQ ID NO: 2, or
      iv) an acetylated, glycosylated, amidated, or phosphorylated naturally occurring allelic variation of SEQ ID NO: 1 or SEQ ID NO: 2, or
      v) an acetylated, glycosylated, amidated, or phosphorylated SEQ ID NO: 1 or SEQ ID NO: 2 having one inserted, deleted, or conservatively substituted amino acid, or
      vi) an acetylated, glycosylated, amidated, or phosphorylated N-terminally truncated or C-terminally truncated SEQ ID NO: 1 or SEQ ID NO: 2, or vii) an acetylated, glycosylated, amidated, orphosphorylated SEQ ID NO: 1 or SEQ ID NO: 2.

2. An N-terminally truncated or C-terminally truncated SEQ ID NO: 1 or SEQ ID NO: 2 having eukaryotic neutral sphingomyelinase enzymatic activity.

3. A medicament containing the isolated eukaryotic neutral sphingomyelinase according to claim 1, together with auxiliary agents.

4. A diagnostic agent containing the isolated eukaryotic neutral sphingomyelinase according to claim 1, together with auxiliary agents.

5. The isolated eukaryotic neutral sphingomyelinase of claim 1, wherein the sequence is SEQ ID NO: 1 or SEQ ID NO: 2.

6. The isolated eukaryotic neutral sphingomyelinase of claim 1, wherein the sequence is a variant of SEQ ID NO: 1 or SEQ ID NO: 2 having eukaryotic neutral sphingomyelinase enzymatic activity, wherein the variant is a naturally occurring allelic variation of SEQ ID NO: 1 or SEQ ID NO: 2.

7. The isolated eukaryotic neutral sphingomyelinase of claim 1, wherein the sequence is a variant of SEQ ID NO: 1 or SEQ ID NO: 2 having eukaryotic neutral sphingomyelinase enzymatic activity, wherein the variant is SEQ ID NO: 1 or SEQ ID NO: 2 having one inserted, deleted, or conservatively substituted amino acid.

8. The isolated eukaryotic neutral sphingomyelinase of claim 1, wherein the sequence is a variant of SEQ ID NO: 1 or SEQ ID NO: 2 having eukaryotic neutral sphingomyelinase enzymatic activity, wherein the variant is -terminally truncated or C-terminally truncated SEQ ID NO: 1 or SEQ ID NO: 2.

9. The isolated eukaryotic neutral sphingomyelinase of claim 1, wherein the sequence is a variant of SEQ ID NO: 1 or SEQ ID NO: 2 having eukaryotic neutral sphingomyelinase enzymatic activity, wherein the variant is acetylated, glycosylated, amidated, and/or phosphorylated SEQ ID NO: 1 or SEQ ID NO: 2.

* * * * *

SEQUENCE LISTING

<160> NUMBER OF SEQ ID NOS: 6

<210> SEQ ID NO 1
<211> LENGTH: 423
<212> TYPE: PRT
<213> ORGANISM: Homo sapiens

<400> SEQUENCE: 1

```
Met Lys Leu Asn Phe Ser Leu Arg Leu Arg Ile Phe Asn Leu Asn Cys
 1               5                  10                  15

Trp Gly Ile Pro Tyr Leu Ser Lys His Arg Ala Asp Arg Met Arg Arg
            20                  25                  30

Leu Gly Asp Phe Leu Asn Gln Glu Ser Phe Asp Leu Ala Leu Leu Glu
        35                  40                  45

Glu Val Trp Ser Glu Gln Asp Phe Gln Tyr Leu Arg Gln Lys Leu Ser
    50                  55                  60

Pro Thr Tyr Pro Ala Ala His His Phe Arg Ser Gly Ile Ile Gly Ser
65                  70                  75                  80

Gly Leu Cys Val Phe Ser Lys His Pro Ile Gln Glu Leu Thr Gln His
                85                  90                  95
```

-continued

```
Ile Tyr Thr Leu Asn Gly Tyr Pro Tyr Met Ile His His Gly Asp Trp
            100                 105                 110

Phe Ser Gly Lys Ala Val Gly Leu Leu Val Leu His Leu Ser Gly Met
        115                 120                 125

Val Leu Asn Ala Tyr Val Thr His Leu His Ala Glu Tyr Asn Arg Gln
    130                 135                 140

Lys Asp Ile Tyr Leu Ala His Arg Val Ala Gln Ala Trp Glu Leu Ala
145                 150                 155                 160

Gln Phe Ile His His Thr Ser Lys Lys Ala Asp Val Val Leu Leu Cys
                165                 170                 175

Gly Asp Leu Asn Met His Pro Glu Asp Leu Gly Cys Cys Leu Leu Lys
                180                 185                 190

Glu Trp Thr Gly Leu His Asp Ala Tyr Leu Glu Thr Arg Asp Phe Lys
            195                 200                 205

Gly Ser Glu Gly Asn Thr Met Val Pro Lys Asn Cys Tyr Val Ser
        210                 215                 220

Gln Gln Glu Leu Lys Pro Phe Pro Phe Gly Val Arg Ile Asp Tyr Val
225                 230                 235                 240

Leu Tyr Lys Ala Val Ser Gly Phe Tyr Ile Ser Cys Lys Ser Phe Glu
                245                 250                 255

Thr Thr Thr Gly Phe Asp Pro His Ser Gly Thr Pro Leu Ser Asp His
                260                 265                 270

Glu Ala Leu Met Ala Thr Leu Phe Val Arg His Ser Pro Pro Gln Gln
            275                 280                 285

Asn Pro Ser Ser Thr His Gly Pro Ala Glu Arg Ser Pro Leu Met Cys
        290                 295                 300

Val Leu Lys Glu Ala Trp Thr Glu Leu Gly Leu Gly Met Ala Gln Ala
305                 310                 315                 320

Arg Trp Trp Ala Thr Phe Ala Ser Tyr Val Ile Gly Leu Gly Leu Leu
                325                 330                 335

Leu Leu Ala Leu Leu Cys Val Leu Ala Ala Gly Gly Ala Gly Glu
                340                 345                 350

Ala Ala Ile Leu Leu Trp Thr Pro Ser Val Gly Leu Val Leu Trp Ala
            355                 360                 365

Gly Ala Phe Tyr Leu Phe His Val Gln Glu Val Asn Gly Leu Tyr Arg
        370                 375                 380

Ala Gln Ala Glu Leu Gln His Val Leu Gly Arg Ala Arg Glu Ala Gln
385                 390                 395                 400

Asp Leu Gly Pro Glu Pro Gln Pro Ala Leu Leu Leu Gly Gln Gln Glu
                405                 410                 415

Gly Asp Arg Thr Lys Glu Gln
            420

<210> SEQ ID NO 2
<211> LENGTH: 419
<212> TYPE: PRT
<213> ORGANISM: Murine sp.

<400> SEQUENCE: 2

Met Lys Leu Asn Phe Ser Leu Arg Leu Arg Val Phe Asn Leu Asn Cys
  1               5                  10                  15

Trp Asp Ile Pro Tyr Leu Ser Lys His Arg Ala Asp Arg Met Lys Arg
                 20                  25                  30

Leu Gly Asp Phe Leu Asn Leu Glu Asn Phe Asp Leu Ala Leu Leu Glu
            35                  40                  45
```

Glu Val Trp Ser Glu Gln Asp Phe Gln Tyr Leu Arg Gln Arg Leu Ser
 50                      55                      60

Leu Thr Tyr Pro Asp Ala His Tyr Phe Arg Ser Gly Met Ile Gly Ser
 65                      70                      75                  80

Gly Leu Cys Val Phe Ser Lys His Pro Ile Gln Glu Ile Phe Gln His
                 85                      90                      95

Val Tyr Ser Leu Asn Gly Tyr Pro Tyr Met Phe His His Gly Asp Trp
             100                     105                     110

Phe Cys Gly Lys Ser Val Gly Leu Leu Val Leu Arg Leu Ser Gly Leu
         115                     120                     125

Val Leu Asn Ala Tyr Val Thr His Leu His Ala Glu Tyr Ser Arg Gln
     130                     135                     140

Lys Asp Ile Tyr Phe Ala His Arg Val Ala Gln Ala Trp Glu Leu Ala
145                     150                     155                 160

Gln Phe Ile His His Thr Ser Lys Asn Ala Asp Val Val Leu Leu Cys
                 165                     170                     175

Gly Asp Leu Asn Met His Pro Lys Asp Leu Gly Cys Cys Leu Leu Lys
             180                     185                     190

Glu Trp Thr Gly Leu His Asp Ala Phe Val Glu Thr Glu Asp Phe Lys
         195                     200                     205

Gly Ser Asp Asp Gly Cys Thr Met Val Pro Lys Asn Cys Tyr Val Ser
     210                     215                     220

Gln Gln Asp Leu Gly Pro Phe Pro Ser Gly Ile Arg Ile Asp Tyr Val
225                     230                     235                 240

Leu Tyr Lys Ala Val Ser Glu Phe His Val Cys Cys Glu Thr Leu Lys
                 245                     250                     255

Thr Thr Thr Gly Cys Asp Pro His Ser Asp Lys Pro Phe Ser Asp His
             260                     265                     270

Glu Ala Leu Met Ala Thr Leu Tyr Val Lys His Ser Pro Pro Gln Glu
         275                     280                     285

Asp Pro Cys Thr Ala Cys Gly Pro Leu Glu Arg Ser Asp Leu Ile Ser
     290                     295                     300

Val Leu Arg Glu Ala Arg Thr Glu Leu Gly Leu Gly Ile Ala Lys Ala
305                     310                     315                 320

Arg Trp Trp Ala Ala Phe Ser Gly Tyr Val Ile Val Trp Gly Leu Ser
                 325                     330                     335

Leu Leu Val Leu Leu Cys Val Leu Ala Ala Gly Glu Glu Ala Arg Glu
             340                     345                     350

Val Ala Ile Ile Leu Cys Ile Pro Ser Val Gly Leu Val Leu Val Ala
         355                     360                     365

Gly Ala Val Tyr Leu Phe His Lys Gln Glu Ala Lys Gly Leu Cys Arg
     370                     375                     380

Ala Gln Ala Glu Met Leu His Val Leu Thr Arg Glu Thr Glu Thr Gln
385                     390                     395                 400

Asp Arg Gly Ser Glu Pro His Leu Ala Tyr Cys Leu Gln Gln Glu Gly
                 405                     410                     415

Asp Arg Ala

<210> SEQ ID NO 3
<211> LENGTH: 1662
<212> TYPE: DNA
<213> ORGANISM: Homo sapiens

<400> SEQUENCE: 3

-continued

```
gcggccgcga ccgccgggga cgagcttgga ggaaaaggaa ccgggagccg cccacccggg      60
ggcgctctcc ggaccccag ggtcctagcg cgcggccctt accgagcctg ggcgcccgga     120
tttcggsagc ggatcgcctt tccggttgg cggcccgcct gattgggaac agccggccgg     180
ttgccggggg aacgcgggag tcgggcccga cctgagccac gcgggcttgg tgcccacctg     240
tgcgcgccgc ctgcgaagaa ggaacggtct agggagaagg cgccgccggc cgcccccgtc     300
cccaccgcgg ccgtcgctgg agagttcgag ccgcctagcg cccctggagc tcccaaacca     360
tgaagctcaa cttctccctg cgactgcgga tcttcaacct caactgctgg ggcattccgt     420
acttgagcaa gcaccgggcc gaccgcatga ggcgcctggg agactttctg aaccaggaga     480
gcttcgacct ggctttgctg gaggaggtgt ggagtgagca ggacttccag tacctgagac     540
agaagctgtc acctacctac ccagctgcac accacttccg gagcggaatc attggcagtg     600
gcctctgtgt cttctccaaa catccaatcc aggagcttac ccagcacatc tacactctca     660
atggctaccc ctacatgatc catcatggtg actggttcag tgggaaggct gtgggctgc     720 tggtgctcca tctaagtggc atggtgctca acgcctatgt gacccatctc catgccgaat     780
acaatcgaca gaaggacatc tacctagcac atcgtgtggc ccaagcttgg gaattggccc     840
agttcatcca ccacacatcc aagaaggcag acgtggttct gttgtgtgga gacctcaaca     900
tgcacccaga gacctgggc tgctgcctgc tgaaggagtg gacagggctt catgatgcct     960
atcttgaaac tcgggacttc aagggctctg aggaaggcaa cacaatggta cccaagaact    1020
gctacgtcag ccagcaggag ctgaagccat ttccctttgg tgtccgcatt gactacgtgc    1080
tttacaaggc agtttctggg ttttacatct cctgtaagag ttttgaaacc actacaggct    1140
ttgaccctca cagtggcacc cccctctctg atcatgaagc cctgatggct actctgtttg    1200
tgaggcacag cccccacag cagaaccca gctctaccca cggaccagca gagaggtcgc    1260
cgttgatgtg tgtgctaaag gaggcctgga cggagctggg tctgggcatg gctcaggctc    1320
gctggtgggc caccttcgct agctatgtga ttggcctggg gctgcttctc ctggcactgc    1380
tgtgtgtcct ggcggctgga ggaggggccg gggaagctgc catactgctc tggacccca    1440 gtgtagggct ggtgctgtgg gcaggtgcat tctacctctt ccacgtacag gaggtcaatg    1500
gcttatatag ggcccaggct gagctccagc atgtgctagg aagggcaagg gaggcccagg    1560
atctgggccc agagcctcag ccagccctac tcctggggca gcaggagggg gacagaacta    1620
aagaacaata aagcttggcc ctttaaaaaa aaaaaaaaa aa                       1662
```

<210> SEQ ID NO 4
<211> LENGTH: 1627
<212> TYPE: DNA
<213> ORGANISM: Murine sp.

<400> SEQUENCE: 4

```
gtgctggtgg aagccgagcc gggaacaagg gaggaacctg taggccgcgg tgcgagaacc      60
caccgaagac ctaagaatct ggaacagtcc acccgagatt ccttccagga ctgccggcgg     120
ctcgcgcacc agcccgggat ttgcagccga ccttcttcc gggtggaagg acggcctttg     180
tcccagtaac gcaggagtcg ccccccaccc ccaaccagct cgcgttcctg ggtcggggca     240
gcgcaggaca gggcaataag cctgtgcgcg caatccgcct cgccgcccctt gctccgaagc     300 actccagcca tgaagctcaa cttttctcta cggctgagag ttttcaatct caactgctgg     360
gacatcccct acctgagcaa acatagggcg gaccgcatga agcgctggg agactttctg     420
```

-continued

```
aacttggaaa actttgatct ggctctcctg gaggaggtgt ggagtgagca ggacttccag    480
tacctaaggc aaaggctatc gctcacctat ccagatgcac actacttcag aagcgggatg    540
ataggcagtg gcctctgtgt gttctccaaa cacccaatcc aggaaatctt ccagcatgtc    600
tacagtctga atggttaccc ctacatgttc catcatggag actggttctg tgggaagtct    660
gtggggctgc tggtgctccg tctaagtgga ctggtgctca atgcctacgt gactcatcta    720
catgctgagt acagccgaca aaggacatc tactttgcac accgtgtggc ccaagcttgg    780
gaactggccc agttcatcca ccacacatcc aagaatgcag atgtggttct attgtgtgga    840
gacctcaata tgcaccccaa agacctgggc tgctgcctgc tgaaagagtg gacagggctc    900
catgatgctt tcgttgagac tgaggacttt aagggctctg atgatggctg taccatggta    960
cccaagaact gctacgtcag ccagcaggac ctgggaccgt tccgtctgg tatccggatt   1020 gattacgtgc tttacaaggc agtctctgag ttccacgtct gctgtgagac tctgaaaacc   1080
actacaggct gtgaccctca cagtgacaag cccttctctg atcacgaggc cctcatggct   1140
actttgtatg tgaagcacag ccccccctcag gaagacccct gtactgcctg tggcccactg   1200
gaaaggtccg atttgatcag cgtgctaagg gaggccagga cagagctggg gctaggcata   1260
gctaaagctc gctggtgggc tgcattctct ggctatgtga tcgtttgggg gctgtccctt   1320
ctggtgttgc tgtgtgtcct ggctgcagga gaagaggcca gggaagtggc catcatcctc   1380 tgcatacccca gtgtgggtct ggtgctggta gcaggtgcag tctacctctt ccacaagcag   1440
gaggccaagg gcttatgtcg ggcccaggct gagatgctgc acgttctgac aagggaaacg   1500
gagacccagg accgaggctc agagcctcac ctagcctact gcttgcagca ggaggggggac   1560 agagcttaag agcttaacaa taaaacttgc ttgacacaca aaaaaaaaaa aaaaaaaaa   1620 aaaaaaa                                                            1627
```

<210> SEQ ID NO 5
<211> LENGTH: 4464
<212> TYPE: DNA
<213> ORGANISM: Homo sapiens
<220> FEATURE:
<221> NAME/KEY: modified_base
<222> LOCATION: (2435)
<223> OTHER INFORMATION: a, t, c, g, other or unknown
<221> NAME/KEY: modified_base
<222> LOCATION: (2437)
<223> OTHER INFORMATION: a, t, c, g, other or unknown
<221> NAME/KEY: modified_base
<222> LOCATION: (2440)
<223> OTHER INFORMATION: a, t, c, g, other or unknown
<221> NAME/KEY: modified_base
<222> LOCATION: (3970)
<223> OTHER INFORMATION: a, t, c, g, other or unknown
<221> NAME/KEY: modified_base
<222> LOCATION: (4036)
<223> OTHER INFORMATION: a, t, c, g, other or unknown
<221> NAME/KEY: modified_base
<222> LOCATION: (4039)
<223> OTHER INFORMATION: a, t, c, g, other or unknown
<221> NAME/KEY: modified_base
<222> LOCATION: (4045)
<223> OTHER INFORMATION: a, t, c, g, other or unknown
<221> NAME/KEY: modified_base
<222> LOCATION: (4076)
<223> OTHER INFORMATION: a, t, c, g, other or unknown
<221> NAME/KEY: modified_base
<222> LOCATION: (4084)
<223> OTHER INFORMATION: a, t, c, g, other or unknown
<221> NAME/KEY: modified_base
<222> LOCATION: (4094)
<223> OTHER INFORMATION: a, t, c, g, other or unknown
<221> NAME/KEY: modified_base -continued

```
<222> LOCATION: (4102)
<223> OTHER INFORMATION: a, t, c, g, other or unknown
<221> NAME/KEY: modified_base
<222> LOCATION: (4103)
<223> OTHER INFORMATION: a, t, c, g, other or unknown
<221> NAME/KEY: modified_base
<222> LOCATION: (4124)
<223> OTHER INFORMATION: a, t, c, g, other or unknown
<221> NAME/KEY: modified_base
<222> LOCATION: (4152)
<223> OTHER INFORMATION: a, t, c, g, other or unknown
<221> NAME/KEY: modified_base
<222> LOCATION: (4164)
<223> OTHER INFORMATION: a, t, c, g, other or unknown
<221> NAME/KEY: modified_base
<222> LOCATION: (4207)..(4208)
<223> OTHER INFORMATION: a, t, c, g, other or unknown
<221> NAME/KEY: modified_base
<222> LOCATION: (4213)
<223> OTHER INFORMATION: a, t, c, g, other or unknown
<221> NAME/KEY: modified_base
<222> LOCATION: (4239)
<223> OTHER INFORMATION: a, t, c, g, other or unknown
<221> NAME/KEY: modified_base
<222> LOCATION: (4265)
<223> OTHER INFORMATION: a, t, c, g, other or unknown
<221> NAME/KEY: modified_base
<222> LOCATION: (4267)..(4268)
<223> OTHER INFORMATION: a, t, c, g, other or unknown
<221> NAME/KEY: modified_base
<222> LOCATION: (4271)
<223> OTHER INFORMATION: a, t, c, g, other or unknown
<221> NAME/KEY: modified_base
<222> LOCATION: (4274)
<223> OTHER INFORMATION: a, t, c, g, other or unknown
<221> NAME/KEY: modified_base
<222> LOCATION: (4277)
<223> OTHER INFORMATION: a, t, c, g, other or unknown
<221> NAME/KEY: modified_base
<222> LOCATION: (4286)
<223> OTHER INFORMATION: a, t, c, g, other or unknown
<221> NAME/KEY: modified_base
<222> LOCATION: (4311)
<223> OTHER INFORMATION: a, t, c, g, other or unknown
<221> NAME/KEY: modified_base
<222> LOCATION: (4320)
<223> OTHER INFORMATION: a, t, c, g, other or unknown
<221> NAME/KEY: modified_base
<222> LOCATION: (4321)
<223> OTHER INFORMATION: a, t, c, g, other or unknown
<221> NAME/KEY: modified_base
<222> LOCATION: (4328)
<223> OTHER INFORMATION: a, t, c, g, other or unknown
<221> NAME/KEY: modified_base
<222> LOCATION: (4334)
<223> OTHER INFORMATION: a, t, c, g, other or unknown
<221> NAME/KEY: modified_base
<222> LOCATION: (4342)
<223> OTHER INFORMATION: a, t, c, g, other or unknown
<221> NAME/KEY: modified_base
<222> LOCATION: (4347)
<223> OTHER INFORMATION: a, t, c, g, other or unknown
<221> NAME/KEY: modified_base
<222> LOCATION: (4354)
<223> OTHER INFORMATION: a, t, c, g, other or unknown
<221> NAME/KEY: modified_base
<222> LOCATION: (4358)
<223> OTHER INFORMATION: a, t, c, g, other or unknown
<221> NAME/KEY: modified_base
<222> LOCATION: (4360)
<223> OTHER INFORMATION: a, t, c, g, other or unknown
<221> NAME/KEY: modified_base
<222> LOCATION: (4367)
<223> OTHER INFORMATION: a, t, c, g, other or unknown
<221> NAME/KEY: modified_base
<222> LOCATION: (4373)..(4375)
<223> OTHER INFORMATION: a, t, c, g, other or unknown
<221> NAME/KEY: modified_base
<222> LOCATION: (4383)
```

```
<223> OTHER INFORMATION: a, t, c, g, other or unknown
<221> NAME/KEY: modified_base
<222> LOCATION: (4389)
<223> OTHER INFORMATION: a, t, c, g, other or unknown
<221> NAME/KEY: modified_base
<222> LOCATION: (4405)
<223> OTHER INFORMATION: a, t, c, g, other or unknown
<221> NAME/KEY: modified_base
<222> LOCATION: (4413)
<223> OTHER INFORMATION: a, t, c, g, other or unknown
<221> NAME/KEY: modified_base
<222> LOCATION: (4417)
<223> OTHER INFORMATION: a, t, c, g, other or unknown
<221> NAME/KEY: modified_base
<222> LOCATION: (4422)
<223> OTHER INFORMATION: a, t, c, g, other or unknown
<221> NAME/KEY: modified_base
<222> LOCATION: (4437)
<223> OTHER INFORMATION: a, t, c, g, other or unknown
<221> NAME/KEY: modified_base
<222> LOCATION: (4445)
<223> OTHER INFORMATION: a, t, c, g, other or unknown
<221> NAME/KEY: modified_base
<222> LOCATION: (4458)
<223> OTHER INFORMATION: a, t, c, g, other or unknown
<221> NAME/KEY: modified_base
<222> LOCATION: (4461)
<223> OTHER INFORMATION: a, t, c, g, other or unknown
<221> NAME/KEY: modified_base
<222> LOCATION: (4463)
<223> OTHER INFORMATION: a, t, c, g, other or unknown

<400> SEQUENCE: 5
gactcgatcc ccgcgaacgc tcgctcgcgc tccgagtctc ttccaggtcg cccttccttg      60
cgaccagcat ttgttctcta tgcccccatc cagccctagg acagaacgtg gaccccccgcc    120 cgccagcgca ggcgacaccg cggcagggg ctgaggtgcg cacggcgtct ggggcgaggg      180
gttacctcag cgatggtctt tgacacctga aagctggagc ttttgaagag ccccaccacc    240
ttcagcttca ggggcggctc gggcggcaac cgcacgtgac atgctggggg cttcgacttg    300
ggccggcacg gctgctgggt ggccatggca gggacagcag agagcccgga acacaaatag    360
tgcgagtcgc cagggcaacc gcgtggctcc tccccgaacg cccgcaaggg gcgggacctg    420
agtgagttcg tgggcggggc ctcgcatcaa cttcaagcct gttgctggtg aagccgagc     480 cgggaacaag ggaggaacct gtaggccgcg gtgcggataa cccaccgaag gacctaagaa    540
tctggaacag tccacccgag attccttcca ggactgccgg cggactctcg cattcagccc    600
gggatttgca gccgaccttc tttccgggtg gaatgacggc ctttgtccca gtaacgcagg    660
agtagccccc cacccccaac cagctcgcgt tcctgggtcg gggcagcgca ggatagggca    720
ataagcctgt gcgcgcaatc cgcctcgccg cccttgctcc gaagcactcc agccatgaag    780
ctcaactttt ctctacggct gagagttttc aatctcaact gctggtaagt aagtgctccc    840
aggcgtgggc tgcagcctcg gagccacctt ccagtcccct ctcgcacatg cctaggaagg    900
aagcaggtct tcttcagccg agctagaccc tgtccttccc gaaccaccaa agtccacatc    960
gcctaaagac cagagcttgg gtggttgcag caatcaccaa agtccctatc atccaaagct   1020
gaggtgatga cagcagtaat cgtcccaaac ctggcccatg tctttccttt taaatgattt   1080
acttttattt tatgtacatt tggtgttttg cctgtatgta tgtctgtgtg aaggtgccag   1140
attctctgga actggagtta cagacagttg taagctgtca tgtgcttgct ggaaattgaa   1200
ctgctgaccc atctcttctg cccctgcgt cctccacccc ttttagggac atcccctacc    1260
tgagcaaaca tagggcggac cgcatgaagc gcttgggaga ctttctgaac ttggaaaact   1320
ttgatctggc tctcctggag gaggtgaggt tgtagggcag gctaggttgg aggagggcag   1380
```

-continued

```
caggcggcag gcggcggcag gaaaacttgt tctgtcttgg gatgaaatcc caagcaagta   1440
tcctcacctt cttcctccag gtgtggagtg agcaggactt ccagtaccta aggcaaaggc   1500
tatcgctcac ctatccagat gcacactact tcagaaggtg aaaagcctgt gttctcagcc   1560
tgttctcaga cgaggaagct ctccaacatt cttgcttgca ccctcgatct tcttcctctg   1620
ggtgtgagaa gagcaggccg tcaccctcat cttgcaaggg ctgctgtctt aggctttgtt   1680
ctggggttga tcttagcagt agagctggga gaccgcggag gggaagaggg ctggctgggt   1740
actcccctcc ttgctcttct ggttattaag caagagttgg ttttcagcgg gatgataggc   1800
agtggcctct gtgtgttctc caaacaccca atccaggaaa tcttccagca tgtctacagt   1860
ctgaatggtt acccctacat ggtaaggatc tcttccctat ccttgctaac acagactgga   1920
cgcagccttc ctggggcctt ggcaggaggg tgtcagtacc ctgagttttt gtcttctctt   1980
gcctgcagtt ccatcatgga gactggttct gtgggaagtc tgtggggctg ctggtgctcc   2040
gtctaagtgg actggtgctc aatgcctacg tgactcatgt gagtggggct agccaggctt   2100
aggcagtggg tcaagcagcc caatgctatg gtggagaaga gacgccacta gttagttctg   2160
ctgcctgggg ataaggcatg ggatcagaag ctagcattgg gcaaggttca cccattccct   2220
gtcacactct gccatgtgac agatgacaag cttgattcag acagccttct ctttgatttc   2280
acctattcca ctttagctac atgctgagta cagccgacag aaggacatct actttgcaca   2340
ccgtgtggcc caagcttggg aactggccca gttcatccag tgtgtgagcc tgggcttgat   2400
gggggctgtg gggtggggac ggggttgagg gatgngnaan ttatccttga agagggcaca   2460
taataaggga agaatttcct ccttgccgct cttcccccaa ctcagccaca catccaagaa   2520
tgcagatgtg gttctattgt gtggagacct caatatgcac cccaaagacc tgggctgctg   2580
cctgctgaaa gagtggacag ggctccatga tgctttcgtt gagactgagg actttaaggt   2640
gagagactgt ttcccaccaa ctccacactt gttccagtct tcctgtctct tagcatccta   2700
gccacctgtt tccctagggc tctgatgatg gctgtaccat ggtacccaag aactgctacg   2760
tcagccagca ggacctggga ccgtttccgt ctggtatccg gattgattac gtgctttaca   2820
aggtcaggct cttattcccg gtgtgccttc tccagtatct tccttcctct gtcactagcc   2880
cacgctttag ttcagctaca gtcttgggcc actgatggct aaagaataga atcctgtcgg   2940
ctggttctct gggagaattt aagcttctcc atgttcttgc tcttcctagg cagtctctga   3000
gttccacgtc tgctgtgaga ctctgaaaac cactacaggc tgtgaccctc acagtgacaa   3060
gcccttctct gatcacgagg ccctcatggc tactttgtat gtgaagcaca gcccccctca   3120
ggaagacccc tgtactgcct gtggtaagca gcatttcctt tgccccctct actttaaggc   3180
agccccgcct ccatcctgac cctccctgc tctacgttct ctctttttcc aggcccactg   3240
gaaaggtccg atttgatcag cgtgctaagg gaggccagga cagagctggg gctaggcata   3300
gctaaagctc gctggtgggc tgcattctct ggctatgtga tcgtttgggg gctgtccctt   3360
ctggtgttgc tgtgtgtcct ggctgcagga gaagaggcca gggaagtggc catcatcctc   3420
tgcataccca gtgtgggtct ggtgctggta gcaggtgcag tctacctctt ccacaagcag   3480
gaggccaagg gctatgtcg ggcccaggct gagatgctgc acgttctgac aagggaaacg   3540
gagacccagg accgaggctc agagcctcac ctagcctact gcttgcagca ggaggggggac   3600
agagcttaag agcttaacaa taaaacttgc ttgacacact ctagtggctc taccttgttc   3660
cttgcagagg catgatggga actgaaggtc agtggccttg tcactgtgtg ctttagagc   3720
```

-continued

| | |
|---|---|
| gttggcctct cacttgcctt ttttgcacac tcccgtctcc tgccagcaca gagcataaac | 3780 |
| cctgttcatg gtcataatcc ttttattgta aacaacgaag cctctgacta agcagtccag | 3840 |
| atggcggagg tacagccctt gtgatggtgt cttgcttacg gggcagggag gcagctaacc | 3900 |
| atcatcttct agccctgggc tcccatctat gcaggcatct ctctgagcct ccgttcctcc | 3960 |
| tggaattggn tcagagcaat cccgcttggt tcaccaacct ccaaacagct tccttaagga | 4020 |
| cctggtttct caaaanggna aggtncgggc ctccggtctt caatangttt tcctaaaaag | 4080 |
| ggangaatga aaanccttaa gnnccaacaa ggggaacccc tggncccaaa aggggacctg | 4140 |
| ggtggtttcc cnttggggcc aaanttatcc caaagggtc caattgaagg gttaaccccc | 4200 |
| caaaaannac ccntttcccc cggaatttcc aaaggtttnc cccccccggc aaaanctccc | 4260 |
| ttggggnncc naanccntgg cccggncttg gcttttcccc ctttcccaag natttcaaan | 4320 |
| nttccctngg aaanccccctt gnttggnaaa accnaatnan gaaccangcc aannnttgcc | 4380 |
| aanaaaccnt ttgggcaaag ggggnaaatt cancaanggg gnaattgggg aaacccntgg | 4440 |
| gttntcccaa agggcccnaa nant | 4464 |

<210> SEQ ID NO 6
<211> LENGTH: 2852
<212> TYPE: DNA
<213> ORGANISM: Murine sp.
<220> FEATURE:
<221> NAME/KEY: modified_base
<222> LOCATION: (1949)
<223> OTHER INFORMATION: a, t, c, g, other or unknown
<221> NAME/KEY: modified_base
<222> LOCATION: (2092)
<223> OTHER INFORMATION: a, t, c, g, other or unknown
<221> NAME/KEY: modified_base
<222> LOCATION: (2181)
<223> OTHER INFORMATION: a, t, c, g, other or unknown
<221> NAME/KEY: modified_base
<222> LOCATION: (2261)
<223> OTHER INFORMATION: a, t, c, g, other or unknown

<400> SEQUENCE: 6

| | |
|---|---|
| accgcggccg tcgctggaga gttcgagccg cctagcgccc ctggagctcc ccaaccatga | 60 |
| agcccaactt ctccctgcga ctgcggatct tcaacctcaa ctgctggtga gtgcgtctgc | 120 |
| ggagtgcggt ctgggggcca ccttccgttc gcacccatgc agccttcctc cccctatccc | 180 |
| gccccacgat ctcagggtgt agggaaaacc cgaacctcca aagtccacat ctggccccag | 240 |
| cgccggtggt cccagcagtc gcctcccctg ccccgctctt cccttcctta ggggcattcc | 300 |
| gtacttgagc aagcaccggg ccgaccgcat gaggcgcctg ggagactttc tgaaccagga | 360 |
| gagcttcgac ctggctttgc tggaggaggt gagattgtgc agcacggtgc ggaacccagg | 420 |
| ctggaggag ggacagaccg tcccactggg gaaagaccaa gcaggcatcc tcaccgcttc | 480 |
| cctcaggtgt ggagtgagca ggacttccag tacctgagac agaagctgtc acctacctac | 540 |
| ccagctgcac accacttccg gaggtgagaa gcccactggc ctgaagcctg ttgtcatccc | 600 |
| aggaggctct tggccctgcc agcccttccc tatcctgcct gcactctcca gtctcctcca | 660 |
| gcctcctctc cctctggatg tgagagaagg agaagggtga accaagaagg tcctatgact | 720 |
| tcagcccatt tcagctttgt tttctggctg ccctatactc ctccaaaggc cgtcgccttg | 780 |
| gttctagggc tagtcccagc agtagaaaaa gaaaaaaata gctgatcaga gctggaagac | 840 |
| aagggagggg aagaaggctg ggtgtctctc cctgttttc tggttattaa gcagggcttg | 900 |
| gctttcagcg gaatcattgg cagtggcctc tgtgtcttct ccaaacatcc aatccaggag | 960 |

```
cttacccagc acatctacac tctcaatggc taccccctaca tggtaaggca gacctttgac    1020
ctcttccacc tcccttcccc acctccagta atacaaggta gaggaggcag ccctctgaga    1080
gctgcagggg atgggcagaa agatggtggc ggtgccctga gtttctatct cctcctgcct    1140
gcagatccat catggtgact ggttcagtgg gaaggctgtg gggctgctgg tgctccatct    1200
aagtggcatg gtgctcaacg cctatgtgac ccatgtgagt gaagctggca gtgcctaggg    1260
ctgggacatg cagcccagtc ctgggacaga gagatggtac ttctctagct ctcatacctg    1320
gggatgaggt gtgggggcaa gatcttataa ggaagcaatg ggcaaggctt atccattgta    1380
taccaaacac catgccaagt gacagacaca ggcttgattc agacataccc ctgggaccct    1440
cagtcttatc tgctgtgatc tcatccatct tgctcagctc catgccgaat acaatcgaca    1500
gaaggacatc tacctagcac atcgtgtggc ccaagcttgg gaattggccc agttcatcca    1560
gtgtgtgagc ctgggcttga atgggaagt gggatgggac ccaggggctg agggtgaaca    1620
aggcccccagt catggggaag agctggtgat ggaagaactc ccgcctcacc aacctggttc    1680
ccccagccac acatccaaga aggcagacgt ggttctgttg tgtggagacc tcaacatgca    1740
cccagaagac tgggctgctg cctgctgaag gagtggacag ggcttcatga tgcctatctt    1800
gaaactcggg acttcaaggt gaggacttgc ctgttacttc cccacctata tccccagctt    1860
ctctccctcc ttctccccca catcctagca tgagccaatg attcccttag ggctctgagg    1920
aaggcaacac aatggtaccc aagaactgnt acgtcagcca gcaggagctg aagccatttc    1980
cctttggtgt ccgcattgac tacgtgcttt acaaggtcag gctcctccct tcaacatgct    2040
ttcatatgct gtgtctcttt gtctactaac ctgtgtagat cctttgctca gntagtctag    2100
tcttggacca ctgatgggtg gaaagtgggg tagccggag ctggttctct gggaagaggc    2160
cctcatatat aagcttctct ntggcccctta cttttcctag gcagtttctg ggttttacat    2220
ctcctgtaag agttttgaaa ccactacagg ctttgaccct nacaggggca cccccctctc    2280
ttgatcatga agccctgatg gctactctgt ttgtgaggca cagcccccca cagcagaacc    2340
ccagctctac ccacggtgag tcacccccac cctttccttg gcccttgccc cgcttgaagc    2400
agcccttcca ctcttgactc tctcctgccc cactgccctg ctctgttgta ggaccagcag    2460
agaggtcgcc gttgatgtgt gtgctaaagg aggcctggac ggagctgggt ctgggcatgg    2520
ctcaggctcg ctggtgggcc accttcgcta gctatgtgat tggcctgggg ctgcttctcc    2580
tggcactgct gtgtgtcctg gcggctggag gaggggccgg ggaagctgcc atactgctct    2640
ggacccccag tgtagggctg gtgctgtggg caggtgcatt ctacctcttc cacgtacagg    2700
aggtcaatgg cttatatagg gcccaggctg agctccagca tgtgctagga agggcaaggg    2760
aggcccagga tctgggccca gagcctcagc cagccctact cctggggcag caggaggggg    2820
acagaactaa agaacaataa agcttggccc aa                                   2852
```